(12) United States Patent
  Cull

(10) Patent No.: US 10,639,189 B2
(45) Date of Patent: May 5, 2020

(54) TREATING CONDITIONS CAUSED BY ABNORMAL GROWTH OF PATHOGENS IN BODY CAVITIES

(71) Applicant: Kimberly Jo Cull, Grove City, OH (US)

(72) Inventor: Kimberly Jo Cull, Grove City, OH (US)

( * ) Notice: Subject to any disclaimer, the term of this patent is extended or adjusted under 35 U.S.C. 154(b) by 1086 days.

(21) Appl. No.: 14/059,843

(22) Filed: Oct. 22, 2013

(65) Prior Publication Data
    US 2014/0058326 A1    Feb. 27, 2014

Related U.S. Application Data

(63) Continuation-in-part of application No. 13/637,496, filed as application No. PCT/US2011/030052 on Mar. 25, 2011.

(60) Provisional application No. 61/717,244, filed on Oct. 23, 2012, provisional application No. 61/318,339, filed on Mar. 28, 2010.

(51) Int. Cl.
    *A61F 7/12*    (2006.01)
    *A61F 7/02*    (2006.01)
    *A61M 31/00*   (2006.01)
    *A61F 7/10*    (2006.01)

(52) U.S. Cl.
    CPC .................. *A61F 7/02* (2013.01); *A61F 7/12* (2013.01); *A61M 31/002* (2013.01); *A61F 2007/0219* (2013.01); *A61F 2007/108* (2013.01)

(58) Field of Classification Search
    CPC ... A61F 7/12; A61F 2007/0063; A61F 7/2007
    See application file for complete search history.

(56) References Cited

U.S. PATENT DOCUMENTS

| | | | | |
|---|---|---|---|---|
| 4,240,436 A | * | 12/1980 | Singleton | A61F 7/10 606/191 |
| 2007/0021809 A1 | * | 1/2007 | Cole | A61F 7/12 607/113 |
| 2008/0269852 A1 | * | 10/2008 | Lennox | A61F 7/02 607/104 |
| 2010/0324635 A1 | * | 12/2010 | Kreck | A61F 7/12 607/105 |
| 2014/0277072 A1 | * | 9/2014 | Suehara | A61M 29/02 606/196 |

* cited by examiner

*Primary Examiner* — Kaitlyn E Smith
*Assistant Examiner* — Yasamin Ekrami

(57) ABSTRACT

A cooling device and method inhibit the infectious growth of pathogens in a body cavity, primarily to cure VulvoVaginal Candidiasis (VVC) and Bacterial Vaginosis (BV) in the vagina, and to reduce biofilms. The device has a shell having an internal chamber containing a freezable or cooling filler that reduces the body cavity temperature. The device may be comprised of an optional coating compound (agent) covering at least a portion of an outer surface of the shell and an optional stainless steel sleeve that covers the shell or optional stainless steel particles that are impregnated into the shell material to enhance both thermal conductance and cooling efficacy. Pathogenic biofilms dissolve and bacteria colony counts decrease at lowered temperatures in body cavities, and infectious, temperature sensitive organisms (fungi, yeast, bacteria, viruses, parasites, and protozoans) become dormant, change morphology, or cease growing under the same lowered body cavity temperatures.

8 Claims, 2 Drawing Sheets

TREATING CONDITIONS CAUSED BY ABNORMAL GROWTH OF PATHOGENS IN BODY CAVITIES

CROSS-REFERENCE TO RELATED APPLICATIONS

This application is a non-provisional of Ser. No. 61/717,244, filed on 23 Oct. 2012. This application is also a continuation-in-part of, and claims the benefit of priority from, pending U.S. Ser. No. 13/637,496, filed on 26 Sep. 2012, which in turn is a national stage entry of PCT/US11/30052, which was filed on 25 Mar. 2011, which in turn is a non-provisional designating the U.S. of provisional patent application Ser. No. 61/318,338, filed on 28 Mar. 2010. Each of the cited applications is incorporated by reference as if fully recited herein.

TECHNICAL FIELD

The present invention relates to a device and method for treating conditions in a body cavity caused by an overgrowth of normal flora, including *Candida* yeast species and certain bacteria, and/or the presence of pathogens, such as 'filamentous' *Candida* yeast species, viruses, bacteria and protozoans. The invention is a cooling or temperature reducing treatment device to cure vaginal infections, including VulvoVaginal Candidiasis (VVC), Bacterial Vaginosis (BV), and to reduce biofilms.

BACKGROUND

Vaginitis is a non-specific term describing symptoms such as irritation and/or inflammation of the vagina that affects millions of women each year. Vaginal infections produce a variety of symptoms, such as discharge, itching, burning, pain, swelling, odor, painful urination or bleeding. Infectious forms of vaginitis can be caused by bacteria, viruses, protozoa, parasites, or an overgrowth of 'filamentous' (hyphal and pseudohyphal) yeast, primarily the *Candida* species. The two most common types vaginal infections are VulvoVaginal Candidiasis (VVC), also known as yeast vaginitis, and Bacterial Vaginosis (BV). Yeast (primarily *Candida albicans*) are dimorphic fungi and are normal inhabitants of skin and body cavities. *Candida* species can become a problem or pathogenic when they become virulent under the influence of heat, a required condition for the pathogenesis of VVC. Other risk factors for the development of VVC besides heat and moisture are sunbathing, swimming, exercise, sexual intercourse, oral sex, tight fitting pants, panty hose, non-cotton crotched underwear, and thongs. Antibiotics, oral steroids, pregnancy, immunosuppressed states, diabetes mellitus, urinary incontinence, and some medications (oral contraceptives) can predispose a woman to recurrent VVC. Beside nutrient restriction, pH changes, CO2, and serum, the requirement for an elevated temperature is essential for the yeast to change size and shape by morphing into their 'filamentous' forms (hyphal and pseudohyphal). These 'filamentous' forms are responsible for the invasive disease state known as VVC. *Candida albicans* (*C. albicans*) and other species may form biofilms as a result of VVC which results in the persistence of the condition and resistance to treatment. The mechanism by which *C. albicans* are able to change their morphology is due to the increased production of HSP 90 (heat shock proteins by *C. albicans* and other species with similar proteins) which occurs as a direct result of elevated temperatures. This 'heat' requirement for yeast to change into their virulent, filamentous forms has remained enigmatic.

Bacterial vaginosis (BV) is the most prevalent cause of infectious vaginitis accounting for about 40-45% of all cases. It is distinguished by a malodorous vaginal discharge that is adherent to the vaginal mucosa of body cavities. While *Gardnerella vaginalis* is associated with the condition, BV is thought to be a synergistic, polymicrobial infection of pathogens, primarily anaerobic, such as *Atopium vaginae, mobiluncus, bacteroides, ureoplasma, mycoplasma, fusobacterium*, among many others. As these pathogens and normal flora multiply, forming a biofilm, they elaborate chemicals and waste products known to elevate the pH and produce the characteristic 'amine' malodorous discharge. It is this biofilm that allows the bacteria of BV to remain resistant to antibiotic treatment and to frequent recurrences. Biofilms ('Surface Slimes') are adherent communities of microorganisms, held together by a polymeric matrix of polysaccharides, proteins, and nucleic acids. Biofilms and their biologic components such as bacteria, yeast, virus, and their metabolic waste products are electrostatically negatively charged. Current studies are underway to find enzymatic or electromagnetic dissolution, so that lactic acid and hydrogen peroxide ($H_2O_2$) can be restored via their production by the normal bacterial flora, known as *lactobacillus*. *Lactobacillus crispatus* predominates in an healthy vagina. The current device will introduce temperature reduction to the tissue and adherent biofilm, to disrupt the biofilm with the optional addition of a coating compound such as pH normalizing or acidifying agent to help normalize the vaginal pH. The elevation in pH from BV probably occurs at a much later stage and is one of the reasons that vaginal applications hydrogen peroxide ($H_2O_2$) and lactic acid have less effect on the persistence of the biofilm, and account for recurrences of BV. Results from research studies show that biofilms exist 'in vitro' at temperatures of 37° C., making biofilms also temperature sensitive, especially at lowered tissue temperatures. Biofilms start to break down at less than 30 C and higher oxygen levels. Therefore, the optional addition of hydrogen peroxide to a cooling device inserted into a body cavity will release oxygen and hydrogen ions that will increase the oxygen content of the vagina which causes the self-destruction of biofilms, will help restore the pH balance (acidification via H+ ion release), and encourage the re-colonization of lactobacilli species in the vaginal epithelium, since this species does not live in biofilms, nor is it temperature sensitive. Lactobacilli produce hydrogen peroxide and lactic acid to keep the vaginal at a normal pH of about 3.5-4.5. Thus, the tissue cooling effect of this intra-vaginal device described in the invention, will simultaneously disrupt biofilms, allow easier penetration of any necessary chemicals or agents, and allow the normal flora of *lactobacillus* species to grow normally and restore the vagina to its normal pH.

The bacteria of BV are both anaerobic and facultative anaerobic and grow best under conditions with little or no oxygen. Fortunately, lactobacilli are facultative anaerobes and tolerate both conditions, but flourish best in the presence of oxygen.

Biofilms on the skin and in body cavities resist removal by conventional soap and water. A mechanism that could prove essential in helping with the treatment and cure of these conditions is that the pathogens' biofilms may be disrupted simply by the mechanical separation of the vaginal (body cavity) walls, the lowering of the temperature of the vaginal tissue, or by applying an agent with an electrostatic positive charge to cause adherence of the negatively charged exopolysaccharide biofilms. For instance, polylysine, a cationic (positively charged) polypeptide used as a food preservative, can adhere to a cell's surface, causing clumping and cessation of protein synthesis, thus preventing spoilage via biofilm formation. BV is dependent on the biofilm for disease persistence and low cure rates of approximately 80%, and biofilms in VVC are less well understood as far as pathogenesis and persistence, but may be a factor in more advanced cases or in persons with underlying conditions such as diabetes, pregnancy, or immune-suppressed states.

Other causes of vaginitis may include vulvodynia and vestibulitis, conditions suspected to be caused by repetitive treatment with antifungal creams and repetitive antigenic exposure to *Candida* yeast species. This infectious destruction of tissue may result in poor healing due to repetitive and over active immune responses, possibly causing permanent 'neuralgias' or autoimmune 'self' destruction of tissue with resultant scarring, recalcitrant pain and burning. Since these conditions (vestibulitis and vulvodynia) are incurable and have poor response to therapies, the present invention has the potential to prevent the need for repetitive chemical anti-fungal drug exposures, thus preventing the occurrence of these conditions in the first place.

There are over eighty-one varieties of yeast, three of which are *Candida albicans, Candida tropicalis, Candida glabrata*, while *C. parapsilosis, C. kefyr, C. krusei* are considered less common causes of VVC. For the most common species, *Candida albicans* accounts for 85-90% of cases of VVC, and the over-the-counter remedies now available will treat and cure this type of yeast only 80% of the time. Current treatment for *C. tropicalis, C. glabrata*, and the others are by physician prescribed antifungal creams only. All current over-the-counter antifungal creams treat only one form of VVC (*Candida albicans*), and take days, not hours to be effective.

The current treatment systems use medicine/drugs (either oral or topical) to treat VVC and BV. Likewise, there are no over-the-counter treatments for other types of pathogens in the vagina like trichomonas, gonorrhea, chlamydia, herpes, *gardnerella* (known to be a factor in BV) or any other, yet to be identified pathogen. The current therapies require the use of anti-fungal or anti-microbial creams/semisolids or oral tablets. When the drug melts in the vagina, it spills out onto the perineum and causes more itching, burning, and pain, exacerbating the symptoms associated with VVC and BV. These emulsions contain many synthetic chemicals and preservatives, which are known to be caustic and allergenic to human skin and mucous membranes. These chemicals, most notably methyl parabens, propylene glycols, cetyl alcohols, sodium lauryl sulfates are caustic to the skin, yet are used routinely in the current antifungal medicines and other therapies (which do nothing more than treat the itch symptom). Most clinicians believe there is an underreporting of these skin reactions, thought to be a result of the over-the-counter manner in which the condition is treated, and due to the fact that the toxic skin reactions mimic the symptoms of VVC, for which a woman seeks relief in the first place. Another problem with OTC and prescription anti-fungal medications is that their mechanism of action (destruction of the yeast cell membrane/wall) results in the release of the cell's toxic contents (enzymes). These released enzymes result in tissue destruction via the mechanism by which *Candida* are able to penetrate tissue and invade the host. This increases the intensity of the symptoms by inflaming the already diseased tissue, prolonging the symptoms for days, before any symptomatic relief is experienced.

Because the woman is confused by the claims of over-the-counter (OTC) medications due to the worsening of her symptoms, she is frustrated as her condition worsens until she either buys more irritating creams or visits her doctor. With regard to BV, there are no OTC remedies for this condition, yet douche manufacturers routinely advocate douching as an effective remedy for vaginal odor, inferring that their products treat this condition. However, BV is known to be more common in women who douche, suggesting that douching chemicals are the actual cause or increase the risk of developing BV, rather than the solution. All obstetricians/gynecologists advise against douching for many well documented scientific reasons (primarily due to increasing the risk of BV, which is a known risk factor for both premature rupture of membranes and preterm births, as well as sexually transmitted diseases), yet the products persist, and are responsible for the recurring nature of the condition. Furthermore, the only treatment options for BV are either systemic (oral) or topical drugs such as Metronidazole and Clindamycin, among others, in the same category of medications. The toxicities for these two medications are noteworthy, with many side effects and drug-drug interactions, as well as possible teratogenicity in pregnancy. These medications are available by prescription only. The invention described herein provides a safe, non-chemical solution for both VVC and BV to help reduce the risk of acquiring vestibulitis/vulvodynia or delivering a premature infant. The cooling device is safer, works faster, and more effectively than chemical alternatives. A non-chemical option that has immediate symptomatic relief and a more effective remedy against all temperature sensitive pathogens and species of *Candida*, and the potential to have an impact on BV via reduction in biofilms and bacterial counts, is the basis for this invention.

Existing medicinal creams add moisture and substances that promote biofilm formation in the vagina, which is counterproductive to curing both VVC and BV. Yeast can survive many environmental conditions, but under normal pH and carbon dioxide levels, additional heat is necessary for yeast to change in size and shape (morphology), grow and multiply to invade tissue, resulting in tissue destruction, enzyme release, and escape from immune cells causing the condition known as VVC. Under normal body temperatures though, the mass destruction of lactobacilli via antibiotics, can result in a flare of VVC as a result of altered (increased pH). *Candida albicans*, which accounts for about 80-95% of VVC outbreaks, can only be grown in a laboratory setting on appropriate growth media at a minimum temperature of 36° C., which is 96.8° F.

Although current drugs do cure VVC infections about 80% of the time, they are not without significant side effects. Oral antifungal medicine also poses significant risks, such as drug interactions resulting in anaphylactic shock or even death. Oral antifungals (fluconazole) used to treat VVC can be compared to using a "bazooka to shoot a mouse"; and, fluconazole only treats one species of yeast, *Candida albicans*.

Additional problems exist with currently available treatments for vaginitis caused by VVC. Current medications, while partially effective, may take 3-7 days to provide relief from itching, burning, swelling, and pain. In addition, both oral and topical drugs may adversely interact with other medications, such as antihistamines, antidepressants, asthma medications and the like. Life threatening anaphylaxis can result from oral systemic medications. Some topical medications can cause toxic skin reactions. Furthermore, the success rate of existing treatment methods range from 60-80% because a chosen drug may not be effective against all of the strains of *Candida* and due to anti-fungal drug resistance, an increasingly common problem due to the over-use or inappropriate use of both topical and oral anti-fungal medications. A need exists for a topical, non-chemical, method of treating both the symptoms and causes of VVC and BV infections within body cavities that is immediate, non-invasive, and effective against all yeast species, the bacterial overgrowth, and biofilms associated with BV, VVC, and other conditions.

Pregnancy is another predisposing condition whereby VVC and BV can cause significant health risks to the mother and the baby such as in preterm, premature rupture of membranes. No currently available medications have been studied in pregnancy for these two conditions, and as such, are placed in Category 'C', meaning unknown risk. A need exists for inhibiting pathologic fungal, microbial, viral, protozoan, and parasitic growth in a body cavity for both pregnant and non-pregnant women.

SUMMARY

The invention in an embodiment is a cooling device to inhibit the pathogenic or infectious growth of an organism and to disrupt a biofilm in a body cavity comprising a shell having an internal chamber containing a freezable or cooling filler, an optional coating compound covering at least a portion of the outer surface of the shell, or impregnated within the material comprising the shell, and an optional stainless steel (SS) sleeve. The shell will be comprised of a thermoplastic polymer or suitable medical grade material and optional SS particles impregnated into the substance of the shell. When the device is inserted into the body cavity (vagina), the frozen or cooling filler absorbs body heat thus cooling the adjacent tissue in gradual manner to disrupt a biofilm and force any temperature sensitive pathogens into dormancy (quiescence) via reversal of morphology, via a 'cold shock response', inhibition of the heat shock response, or via some 'other' yet to be described molecular or biochemical mechanism.

In an embodiment, the coating compound comprises a gel carrier and an agent. The gel carrier comprising a hydrogel having covalently linked biopolymer chains. The hydrogel swells upon contact with fluid causing degradation of the gel carrier such that the agent is released from the coating compound in a controlled manner and contacts the tissue wall of the body cavity. The agent is one, or a combination of, a pH normalizing, pH acidifying, anti-microbial, anti-fungal, anti-parasitic, anti-protozoan, herbal, hormonal, steroidal, non-steroidal, oxygen releasing (H2O2), anti-inflammatory, anti-oxidant, antiseptic, electrostatically charged, or probiotic substance, chemical, ingredient, or material. The gel carrier and agent may be pre-applied or mixed and applied to the shell prior to insertion into the body cavity. In an embodiment, the compound is inserted separately from the device, immediately prior to or after insertion of the device into the body cavity such that the device acts both to retain the compound in the body cavity for an undetermined duration of time to take effect and cause temperature reduction in the cavity. The coating compound may comprise a gel-forming solution or hardener to produce the coating. The coating compound may be liquid, particulate or powder, may be impregnated into the shell material either during or subsequent to the manufacturing process. The coating compound may actually dissolve and be released from the shell surface upon contact with the tissue.

When the device is inserted into the body cavity, the freezable or cooling filler cools the body cavity via passive thermal conductance or transference of heat in order to disrupt the biofilm, allowing the optional coating compound (agent) better access to the pathogen(s) and to facilitate the disruption and breakdown of the biofilm. In the embodiment, the shell comprises SS particles to prolong the cooling effect and to facilitate the conductance of heat away from the body cavity tissues.

In an embodiment, the shell is enclosed inside a SS sleeve with the coating compound applied to the exterior of that SS sleeve. The gel carrier is comprised of a hydrogel having a network of covalently linked biopolymer chains. The hydrogel swells upon fluid contact causing degradation of the gel carrier such that the agent is released from the coating compound in a controlled release manner and contacts the tissue walls of the body cavity, and the SS provides a longer, more steady duration of cooling that results in biofilm disruption and pathogen growth suppression, allowing more effective 'agent' access to the pathogens.

To use the device in order to inhibit the growth or reverse *Candida* species morphology and to disrupt biofilms created by organisms in a body cavity, a user first cools or freezes the device, or allows for a mixture of chemicals to create an endothermic reaction, which has an optional SS sleeve covering the shell, which has an internal chamber containing a cooling or freezable filler. The user then applies an optional coating compound and covers at least a portion of the outer shell of the cooling device or SS sleeve surface with the compound and inserts the device (with or without the SS sleeve) into the body cavity. After the device reaches approximately the same temperature as the body cavity, the user removes the device from the body cavity and repeats the process until the infectious conditions have abated or until sufficient research is generated to determine the appropriate duration of use and dosage intervals.

The present invention is a cooling device, with an optional compound delivery or retention function for body cavities to force *Candida* species and other potential temperature sensitive pathogens into the dormant, non-disease state, to reduce an overgrowth situation, and to disrupt biofilms. Cooling of a body cavity to temperatures of less than 30 C causes the disintegration of biofilms which are contributors to the disease state of VVC, BV, and other pathological conditions of the body cavity. The device is useful to treat problems such as VVC, an infection of the vagina caused by the filamentous growth of *Candida* species, chemical dermatitis of the vagina and vulva, BV, an overgrowth of gram negative, anaerobic bacteria (previously defined as BV), and any associated biofilm mediated conditions. The device may have similar utility for other temperature sensitive pathogens of the vagina, such as trichomonas and herpes, or for other body cavities. The present invention inhibits or reverses pathological 'filamentous' fungal (*Candida* species), may prevent or treat other microbial infections such as BV, parasitic, protozoan, and viral infections while reducing biofilm formation simultaneously. The present invention's coating compound may be pH neutralizing, pH acidifying, may contain inactive ingredients, may contain anti-inflammatory such as aloe, anti-oxidant compounds, hormones, steroids, non-steroidal agents, herbs, anti-septics such as H2O2, lactic acid, anti-microbial, anti-viral, anti-parasitic, anti-fungal, anti-protozoan, electromagnetic, natural stabilizing agents or artificial preservatives, oils, vitamins, or minerals as components of the coating compound housed in a gel, emulsion, powder, particles, creams, or emulsions or be impregnated into the shell of the device.

The invention addresses the optional application of a coating compound, medication, or topical chemical as described above, which aids in curing the infection in the body cavity, such that in conjunction with the cooling component which disrupts biofilms and reverses infectious morphologies, helps the coating compound to be more effective, at lower dosages and with less duration of exposure, allowing the normal host mechanisms to heal and repair the tissue faster, and to reduce the severity of the symptoms, such as itching, burning, swelling, and pain. The normal inhabitants of the vagina (*lactobacillus*) can repopulate more quickly, ensuring a normal pH and healthy ecosystem of the body cavity.

The device, comprising a shell, with or without a removal means (string or loop, for example) whereas the expulsion of the device can be accomplished by a Valsalva maneuver or 'bearing down' as is the case with normal ambulation, coughing, or lifting. The shell, with an internal chamber filled with a freezable or cooling filler, and an optional coating compound for the shell, may also be covered by a SS sleeve whereby the hollow sleeve chamber is filled with ambient air until it is placed over the shell of the device. The SS sleeve would be important to facilitate a prolonged cooling effect (enhanced thermal conductance), thus improving the overall effectiveness in curing the infection and reducing biofilms in body cavities. In such case of a SS sleeve, the optional coating compound would cover the exterior surface of the SS sleeve.

When the shell with the cooled or frozen filler is inserted into a body cavity, the device (invention) cools the body cavity to a temperature that causes the filamentous forms of *Candida* species to reverse back to their yeast or bud shape, which is the dormant, non-disease forming state and disrupts the biofilms which are associated with VVC and BV, as well as biofilms associated with douching and other chemicals used in feminine hygiene products and soaps. This allows the non-temperature dependent *lactobacillus* species to recolonize the vagina to normalize the pH and allow the healing process to take place naturally. The filler is not in direct contact with the body cavity walls, but is separated by the shell's wall thickness which is important with respect to the rate of transference of heat. The material of the filler is any cooling or freezable substance, including but not limited to a liquid such as saline, distilled or bacteriostatic water, a gas, a solid or semi-solid, or a gel or hydrogel, or via the mixing of two or more substances to cause an endothermic reaction which has heat absorptive and cooling effects on a body cavity.

The shell's chamber, which contains the filler, may comprise two or more compartments separated by breakable walls. Each compartment is filled with a substance such that when the wall is disrupted or broken, the substances combine to create a cooling effect via the endothermic reaction. This mixed substances, now the filler once used, can be re-cooled or frozen for re-use inside the shell and inserted into the body cavity to reduce the tissue temperature on another occasion. The removal means is any mechanism or attachment to the shell such as a string, cord, loop, stalk, knob, button, ball, and the like, that when grasped and pulled, will result in complete removal from the body cavity. Or, in the case of no such attachment, removal will be accomplished by simple Valsalva, coughing, or bearing down.

In the embodiment, an optional external (to the body cavity) cooling component or extension may be attached to the shell after insertion, be intrinsic to the shell's design, or be a completely separate apparatus in order to apply cooling or cause heat transfer from the contiguous vulvar, clitoral, and perineal tissue which also harbors the infectious condition such as *Candida* or other pathogenic organisms of these regions. The external cooling component is comprised of a shell with a freezable or cooling filler inside an internal chamber as described in above.

In an embodiment, the invention treats infectious diseases caused by pathogens such as *Candida* species (VVC), fungus, anaerobic and facultative bacteria (BV) and their associated biofilms and those biofilms that may be a result of chemicals used in douching, feminine hygiene products, soaps, body washes, and ingredients found in medications or products used in body cavities or surfaces. When the shell with the cooling, freezable, or frozen filler is inserted into a body cavity, the filler gradually warms or thaws via passive thermal conductance such that the body cavity's tissue temperature is lowered which inhibits further virulent growth and reverses *Candida* species' morphology to the dormant, non-disease causing morphology, reduces biofilms, allows for the optional addition of a coating compound to enhance the device's (invention's) efficacy and may serve as a substance retention or delivery device in order for that compound to exert additional therapeutic effect, at lower dosages, with reduced duration of exposure, and with reduced side effects or toxicities. The invention is an optional substance retention device, whereby it limits the spillage of any compounds onto the contiguous tissues (perineum, vulva, clitoris) where the nerve supply is abundant thus resulting in the painful and bothersome side effects associated with many compounds and chemicals. The optional SS sleeve to cover the invention's shell enhances thermal conductance, duration of cooling effect, and efficacy.

As used herein, "approximately" means within plus or minus 25% of the term it qualifies. The term "about" means between ½ and 2 times the term it qualifies.

The compositions and methods of the present invention can comprise, consist of, or consist essentially of the essential elements and limitations of the invention described herein, as well as any additional or optional ingredients, components, or limitations described herein or otherwise useful in compositions and methods of the general type as described herein.

Numerical ranges as used herein are intended to include every number and subset of numbers contained within that range, whether specifically disclosed or not. Further, these numerical ranges should be construed as providing support for a claim directed to any number or subset of numbers in that range or to be limited to the exact conversion to a different measuring system, such, but not limited to, as between inches and millimeters.

All references to singular characteristics or limitations of the present invention shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

Terms such as "top," "bottom," "right," "left," "above", "under", "side" "front" and "back" and the like, are words of convenience and are not to be construed as limiting.

DETAILED DESCRIPTION

Reference will now be made in detail to the exemplary embodiments of the invention, examples of which are illustrated in the accompanying drawings.

Figure 1:
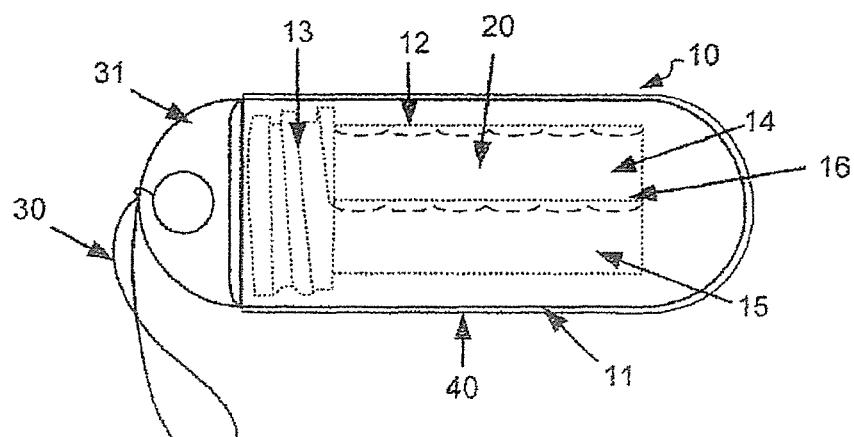
FIG. 1 is a see-through view of an embodiment of the invention showing the chamber 12 for the filler 20.

In accordance with an embodiment of the present invention as shown in FIG. 1, the device is comprised a shell 10, a filler 20 and an optional coating compound 40. The shell of the device, once cooled or frozen, is optionally housed in a stainless steel sleeve (not shown). The device may include removal means 30 or 31. The shell is preferably made from silicone, medical grade thermoplastic polymers, or stainless steel (SS) and comprises an external wall 11, enclosing a chamber 12 that is sealed with a plug 13. In the case of heat sealing after filling the chamber, there is no plug or cap and the device is a single unit. The chamber may have one or more compartments 14, 15. The compartments are formed with breakable wall(s) 16 between or among them. The filler 20 is a non-toxic substance, such as but not limited to, saline, distilled water, a gel, or gas, and the like. The filler may comprise several components that are housed apart in the compartments until use. In an embodiment, the removal means 30 (if needed) is a string or cord firmly attached to the shell or to 31.

Figure 3:
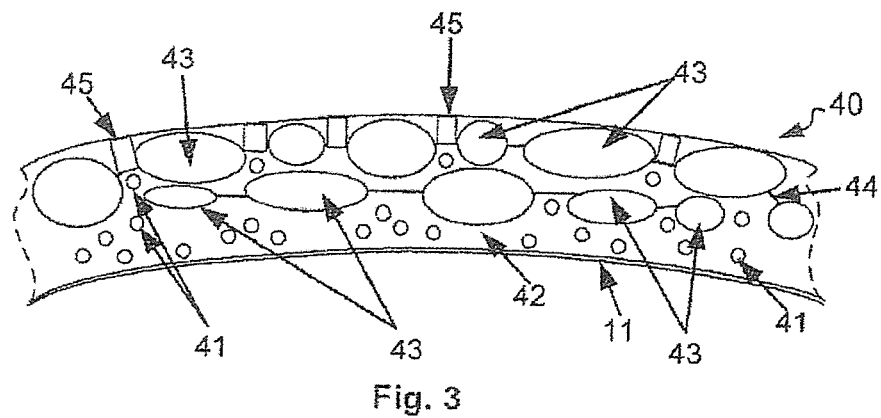
FIG. 3 is a diagrammatic side view of the coating compound of the invention showing the polymer and the agent.

As shown in FIG. 3, the coating compound 40 comprises a gel carrier 42 and an agent 41. The agent is a pH normalizing or acidifying agent, anti-microbial, anti-fungal, steroidal, non-steroidal, hormonal, anti-oxidant, anti-inflammatory, herbal, anti-septic, electromagnetic, oxygen releasing, or probiotic, or combination thereof. The compound is applied to the shell prior to insertion or inserted separately by an applicator prior to the device's body cavity placement. In the case of electromagnetic coatings, they may be applied during the manufacturing process, or impregnated into the shell material. Alternatively, the coating compound is applied to the external surface of the SS sleeve (not shown).

The compound comprises a gel carrier 42 that is relatively soft. In an embodiment, the invention uses a gel-forming solution with a hardener to produce the coating. The aqueous gel is relatively soft so that the aqueous gel does not adversely affect the device. In an embodiment, the coating covers all of the device. Alternately, only portions of the external wall 11 are coated (with either a coating compound or stainless steel sleeve or particles).

The gel carrier is a chemical hydrogel having a network of biopolymer chains 43 covalently linked at strategic connection sites. The chemical hydrogel is created by using crosslinkers 44 to covalently bridge the biopolymers at specific selected sites, typically by reaction with small molecules. Upon contact with water, the hydrogel hydrates and swells until an equilibrium state is reached, which depends on the extent of the crosslinking. The swelling process is governed first by water binding at the hydrophilic sites of the biopolymers, followed by the entrapment in the gel network.

Figure 3A:
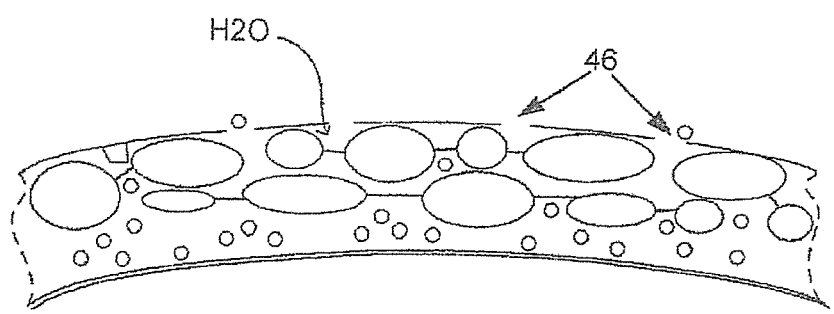
FIG. 3a is a diagrammatic side view of the coating compound beginning to break down and release agent.

As shown in FIG. 3a, diffusion of the agent occurs predominantly through the void spaces between the polymer chains. Addition of plasticizer 45 (FIG. 3, both type and concentration) influences release of the agent 41. Plasticizers reduce polymer-polymer chain secondary bonding and provide mobility for the agent. Plasticizer leach out of the polymer results in pore formation 46 for release of a portion of the agent 41. Subsequent release of agent is based on diffusion through the polymer. Polyurethane, poly(ethylene vinyl acetate), and polydimethylsiloxane are polymers used in the invention. Biodegradable polymers, the polyesters, which consist mainly of poly(caprolactone), poly(lactic acid), poly(glycolic acid) and copolymers of lactic and glycolic acids are used in the invention. As depicted in FIG. 3a, agent 41 is initially diffused by eroding of the compound. Polyanhydrides and polyorthoesters degrade only at the surface of the polymer, resulting in a release rate that is proportional to the surface area of the device. Polylactic acid and polylactic-co-glycolic acid are used for erosion to allow an even rate of agent delivery.

Figure 4:
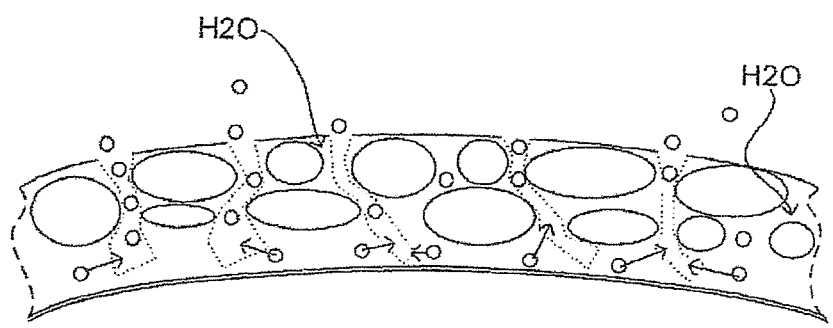
FIG. 4 is a diagrammatic side view of further breakdown of the coating compound and the continued release of the agent.

The release of the agent from the compound is initially rapid, followed by a phase where the agent diffuses more slowly out of the compound and then the remaining agent is released due to the degradation of the polymer (FIG. 4). The extent of the initial release is controlled by plasticizers. High burst release is minimized by hydrophobic plasticizers; the opposite effect is achieved by hydrophilic plasticizers, which leach out of the polymer. The release of the agent depends on the polymer molecular weight parameters. Low molecular weight polymers or oligomers are preferred. Star-like copolymers of hydroxyacids with polyhydric alcohols, such as pentaerythritol, mannitol, glucose, polyvinyl alcohol and others are also used because the branched carriers dictate the agent release by the degree of branching.

In an embodiment, the coating compound containing an agent comprises a gel, liquid or powder coating that may contain an anti-fungal, anti-viral, antibiotic, anti-microbial, anti-parasitic, anti-protozoan, pH normalizing or acidifying (i.e. lactic acid), oxygen releasing agent (i.e. hydrogen peroxide), electromagnetic, alone or in some combination. Agents are further selected from the group LAE (lauramine arginine ethyl ester is a detergent-like agent and safe for food use), polylysine, stainless steel (confluent sleeve or as particles impregnated into the shell), steroidal, non-steroidal, hormonal, anti-oxidant, anti-inflammatory, antiseptic, or probiotic, alone or in combination. The device keeps the agent pressed against and penetrating the tissue walls within the body cavity, making the combination of a cooling device with an agent possibly more efficacious (than either could perform alone), with less spillage onto the outside perineum where it would be less effective or potentially caustic to the skin. Because the device retains the coating compound (agent) inside of the body cavity, less concentrated dosages and shorter duration of exposure to these compounds will prove beneficial in reducing side effects and toxicities and potentially improving efficacy. The coating compound may be for the purpose of lubrication or ease of insertion alone or in addition to the above listed purposes.

Figure 2:
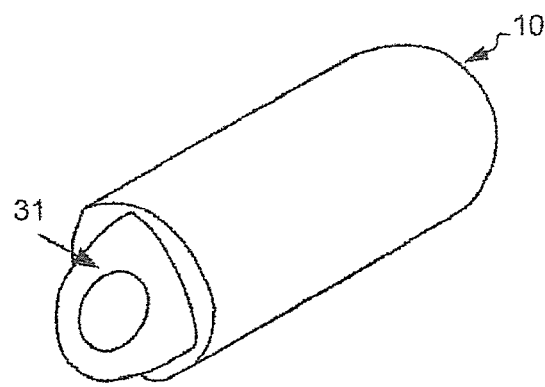
FIG. 2 is a perspective view of an embodiment of the invention.

In an embodiment shown in FIG. 2, an optional removal means comprises an attachment 31. The attachment is an extension of the plug or an extension of the shell that is graspable such as a cord, bulb, stalk, button, loop attached to the plug or as an extension of the shell. In an embodiment, the attachment is a loop formed from cotton or suitable biocompatible material, including the same material as the shell.

In an embodiment, the plug 13 is screwed into threads or snapped on at the opening of the chamber after the filler is inserted, then sealed completely. The device further comprises a storage container (not shown). The device is packaged in according to GMP and FDA/CE marking requirements and may or may not be sterile as in many other class I and II devices for intravaginal use, such as tampons. There will be detailed instructions/explanation of method of use, and safety guidelines.

The silicone or medical grade thermoplastic polymer shell is constructed in various forms, shapes, or sizes to accommodate varying body cavity shapes and sizes. In an embodiment, the shell is of similar fashion to the current silicone breast implants or made of material currently used in pessaries, vaginal dilators, or menstrual cups. A Stainless Steel (SS) sleeve may be used alone or in combination, and it may represent a confluent surface or separate particles impregnated into the material of the shell. In an embodiment, the shell is more rigid, similar to silicone used in re-useable ice cubes which are either filled with distilled water, saline, or semi-solid hydrogel material. The hollow chamber of the device is filled with saline, distilled water, gas, hydrogel gel or other similar material that can either be frozen or cooled sufficiently (possibly through the mixing of two substances creating an endothermic reaction) to effect a cure of the condition it is designed to treat/cure/or improve. The silicone, thermoplastic polymer, or other suitable material (with or without stainless steel particles or SS sleeve) is shaped to accommodate the shell of the device and may be a cylinder, a tube, oblong in shape, egg-shaped or any variety of configurations with varying lengths, widths, diameters, and circumferences. Visualize a tampon for instance, a bullet, or a hotdog. Also, some of the devices will be shaped with an additional component—visualize a pacifier—to cool the external region of the body cavity. The coating compound or SS may be applied to any part of the device.

The size of the invention (device) will be determined by the optimal size to produce the safest, fastest, and most comfortable cure. There may be multiple sizes for different sizes and shapes of body cavities. A removal material may be a string of approximately 1-6 inches and attached to one end of the shell. In a reusable embodiment, the removal material is washable. In a disposable embodiment, the string is any inexpensive method of retrieving the device from the body cavity or positioning the device within the cavity, and may be composed of but not limited to, paper, cloth, plastic, or cotton string/cord and the like. In the case of a reusable device, the coating compounds are packaged in separate containers or pouches with directions for mixing and application.

In an embodiment, the invention comprises a shell, with or without a coating compound, a freezable or cooling filler inside the shell's chamber, and the ability to remove and store the device, and an optional stainless steel sleeve to cover the shell. Additional mechanism/materials are optional for the purpose of inserting the device or accomplishing the intended goals of the invention. The cooling or frozen filler substance can be liquid, gaseous, semisolid or solid, or gel. Additional materials can be used and modifications may be made to the device depending on cost, safety, biocompatibility, effectiveness, and other medical considerations.

The silicone or other suitable material used to construct the shell's shape is formed into a cylinder, tampon shaped, bullet shaped, or hotdog shape, rounded on one or both ends, or may be completely round, malleable, or changeable, but the size and shape are largely irrelevant as long the device accomplishes the intended purpose of the invention as defined in earlier passages and as stated in the Claims Section. The shell has a hollow internal chamber that contains the filler that can be frozen, made cold via the chemical reaction by mixing of two or more substances, or in the case of gas, may be inert. In an embodiment, the freezable substance is saline or an hydrogel, although any other suitable material or substance may be used that permits cooling or heat transference in body cavity tissues. The optional removal means can be cleaned or sanitizable by routine household means in the case for reusable devices. In an embodiment, the removal means is a string. In an embodiment, the removal means is a ring or extension of flexible material attached to one end of the shell. The stainless steel sleeve will be made in one or more sections so as to cover the shell partially or completely. SS particles may be impregnated into the shell material to improve heat conductance and cooling capacity.

Saline, water, or hydrogels, (such as CMC gels used in breast implants since 1994) are used as filler for the shell because of the inert properties and proven safety when used inside the body. In manufacturing, the filler is added to the chamber in the shell and the shell is sealed, either as a single or multiple piece device.

As used herein, the words filler includes any substance or material that can be rendered frozen or sufficiently cold to accomplish the goal and novelty of the invention. In an embodiment, the filler is a non-toxic polymer gel, such as a medical grade gel refrigerant or biodegradable hydrogel. Saline is distilled water with dissolved sodium chloride (NaCl) or salt. The internal component of the device must be able to made cold, cooler, or frozen when removed from a freezer or a cooling apparatus, or when two or more materials mixed together to produce an endothermic reaction, rendering the device cool or cold enough to be able to conduct heat away from warmer adjacent body cavity tissue via heat absorption. Saline or analogous/similar substance/material (when frozen or cold) is the crux of the design of this device, and is not to be in direct contact with the vaginal tissue. In the case of a SS sleeve, the temperature of the SS sleeve may be room temperature, prior to placement over the shell of the cooling device in a sequential manner of use. The frozen or cooled saline, water, or hydrogel is the reason that this device is effective and the silicone (or shell material) is firm enough to be placed in the vagina. Materials such as silicone and thermoplastic polymers do not freeze when subjected to the temperatures in the common freezer. However, if the shell is impregnated with stainless steel particles, then the device may be placed into the refrigerator, or freezer, to cause the same cooling, heat absorbing capacity. If the cooled or frozen device is too hard or stiff when removed from the freezer, a quick exposure to tap water will soften it. However, the device needs to be in a solid/semi-solid/frozen condition or sufficiently firm in order for it to be inserted easily into the body cavity. The device, once inserted will be slightly visible or palpable at the hymenal ring or introitus, or may be completely inserted depending on the comfort level of the user. The closer the device is to the opening of the body cavity, the more heat absorption can be derived from the external skin surface of the body cavity which helps cure both the internal and external reservoir of pathogens. Deeper insertion is possible or likely to occur as a result of the body cavity's musculature and movement of the device's carrier. The vagina and vulvar tissue are innervated differently, with less 'sensation' noted deep to the hymenal ring within the vagina. However, it is within the vagina that the *C. albicans* and pathogens multiply best, and where biofilms stay intact. So, it is the length, width, diameter, circumference, and surface area of the device that must be sufficient to accomplish cooling far enough into the vaginal cavity to effect a cure for the conditions described herein. However, the device should not be adjacent to the cervix for comfort reasons, unless it is determined by research that it is safe and efficacious to allow cervical contact. Cramping might occur if the device came into contact with the cervix due to its innervation. In an embodiment, the fluid or filler is a cold pack comprised of a shell having several compartments separated by breakable barriers. Each of the compartments contain an ingredient which, when mixed with another ingredient(s), chemically react together to create a cooling effect (endothermic reaction). One or more of the ingredients may be a liquid, powder, a semi-solid, gas, or solid substance. For appropriate use, the barriers are broken allowing the contents to be mixed together.

Alternatively, the filler (saline, water or hydrogel) is an encased instant cold gel pack comprised of ingredients in breakable compartments, that, when mixed together, form a cooling gel. The addition of the gel allows for later use. For re-use, the device is place in a freezer, refrigerator, or cooling apparatus until needed.

The device has no active energy source. The human body temperature of the body cavity provides the warmth or heat to thaw the cooling or frozen filler, thereby slowly cooling the adjacent tissues. The device acts to inhibit 'filamentous' yeast and bacterial overgrowth in body cavities by passive heat absorption (thermal conductance) from the body cavity or vaginal tissue (which is typically about 37° C. or 99° F.) through the shell walls of the device to slowly melt the cooled or frozen filler gel, substance, etc. During treatment (about 45 minutes), the temperature of the tissues of the body cavity near the inserted device drop to approximately 68°-72 F within the first 10 minutes, then slowly rises to approximately 78-80° F. by about 30 minutes, approximately 91-94° F. by about 45 minutes, and about 98° F. at about 55 minutes as the filler thaws from heat absorption or thermal conductance. The treatment time and degree of tissue cooling (to be determined) is sufficient to force yeast into a dormant yeast 'bud' morphology and out of the 'filamentous' virulent morphology, and to reduce bacterial multiplication and biofilm persistence found in conditions known as VulvoVaginal Candidiasis (VVC) or Bacterial Vaginosis (BV). Different duration of contact and amount of thermal energy transfer may be used for altering the temperature inside the body cavity, depending on the desired clinical effects. These temperatures are used as an example of reducing the 'filamentous' forms of yeast (primarily *C. albicans*) causing it to morph back to the yeast 'bud' morphology which is the dormant, non-disease causing state, and thus does not result in the release of the toxic cell contents which occurs when anti-fungal chemicals destroy yeast cell walls. However, in the case that research determines that the invention's cooling properties does result in *Candida* wall disruption, then the mechanism of action is similar to chemical anti-fungal therapies, but without the delayed onset of action and side effects of chemicals. Furthermore, anti-fungal chemicals contribute to the formation of biofilms whereas this invention's cooling device reduces biofilm formation and persistence, without adding chemicals, unless a coating compound is added. The coating compounds, for the purpose of this invention, will be non-biofilm producing. Biofilms disintegrate at a temperature less than 80° F. The device will render the tissue cooler than this temperature for approximately 30 minutes, or longer depending on final volume and properties of the selected filler, and desired clinical outcomes or efficacy which future research studies will elucidate.

The device is effective because it renders the surrounding tissue cooler, and thus the temperature sensitive pathogens are unable to replicate/reproduce/persist in a biofilm that cause the disease or conditions. The inhibition, blocking or reversing of filamentous yeast morphology and disrupting biofilms caused by both yeast and pathogenic (anaerobic bacteria) allows the body cavities' normal flora (lactobacilli) to reestablish and suppress the yeast and anaerobic bacteria by putting them into a dormant, non-invasive, or non-filamentous form as when the temperature in the body cavity returns to normal. The yeast and bacteria remain in either normal 'physiologic' levels or dormant morphologies in non-diseased states (non-biofilms) unless conditions arise to initiate another growth cycle such as with another temperature elevation, pH changes, douching, antibiotic use, or exposure to douches or sexual events. The addition of SS particles or stainless steel sleeve covering the device's shell helps the biofilm to dissolve as a result of prolonged temperature reduction of the surrounding tissue.

The cooling effect will also ameliorate the disturbing symptoms of yeast vaginitis (or other similar conditions, including BV). Itching, burning, and swelling respond to coldness by causing the capillaries to shrink (constrict) thus preventing the egress of a fluid into the tissue which results in swelling and pain. Coldness/ice packs are effective ways to reduce swelling caused by inflammation. With regard to the chamber being filled with a substance, the saline/hydrogel, or distilled water will remain in the solid state longer (absorb heat slowly) than tap water and will freeze more quickly that water. Also, saline, hydrogel, and distilled water are sterile and safe.

The process would be similar to the production of hydrogel or saline filled silicone breast implants and/or re-useable ice cubes (made of a silicone shell or thermoplastic polymer), with the addition of a flexible string-loop-like material for easy removal of the device. If the device is not to be a reusable device, then the string could be the same as a tampon (i.e. cotton).

Other substances can be used to fabricate this device such as using a tampon-like material (fiber) natural or synthetic, but not comprising an enclosure (shell). However, any absorbent material will result in moisture being introduced and wetness will make this unsuitable for most women (besides aggravating the condition it is designed to treat), including latex or other non-medical grade rubber or aromatic plastic materials, due to the possibility of allergic reactions. The sleeve will be constructed of a medical grade stainless steel.

The user would keep the device(s) in a frozen or cooler state until needed, unless the mechanism of cooling is via the mixing of room temperature materials. The SS sleeve will be kept at room temperature, but if the SS particles are impregnated into the shell of the device, then it will be placed into a freezer, refrigerator, or cooling apparatus. Then, the device would be removed from the storage container and placed under tap water for 3-5 seconds or less, then inserted into the body cavity (vagina or analogous body cavity). The rounded end is inserted first, so that the removal means (if present) is closest to the body cavity opening. The device may be adjusted using the attachment or the removal means for comfort. The device remains in the body cavity for less than about 1 hour or until no additional cooling sensation is noticed or experienced, and is then removed. A subsequent new or re-usable frozen or cooling device would be inserted at that time, if needed. This could be continued until the user was not experiencing any itching or discomfort, possibly requiring repetitive episodes of treatment every 4-6 hours, depending on the severity of the symptoms and length of time needed to cure the infection. Future research will determine the optimal treatment duration, level of tissue cooling needed, and frequency of treatment to cure VVC and BV. Once the re-usable device has been used, it is removed from the body cavity, rinsed in warm, soapy water, dried and replaced back in the storage container and placed back into the freezer or disposed of but, not by flushing. The SS sleeve may be reusable after being washed and dried.

The invention treats a condition called VVC caused by yeast (all genus/species or yeast, specifically, *Candida albicans, Candida-tropicalis*, and *Candida glabrata*) and may be effective against other microbes, such as protozoa, viruses, parasites, and bacteria, especially BV associated pathogens and biofilms. It stops the virulent growth and dissolves biofilms via cooling of the body cavity.

The addition of the coating compound may increase the efficacy of the cooling device while the cooling inhibits growth of the infectious pathogen, and disrupts biofilms. The device achieves results by lowering the temperature in the body cavity thus limiting the 'filamentous' growth of yeast, pathogenic bacterial growth, and other microbes, while dissolving biofilms. The agent in the coating compound adds anti-fungal, anti-viral, antibiotic, anti-microbial, anti-parasitic, anti-protozoan, pH normalizing or acidifying capabilities, steroidal, non-steroidal, hormonal, anti-inflammatory, anti-oxidant electromagnetically charged, anti-septic, oxygen generating, or probiotics, either alone or in combination to the cooling, tissue temperature reducing properties of the device.

The present invention also ameliorates the concomitant symptoms such as burning, itching, swelling, and pain associated with both BV, VVC, vaginal atrophy, radiation induced vaginitis, and dyspareunia from multiple causes. However, this is not considered a novel or unique aspect of the invention since all cooling packs ameliorate inflammatory conditions, irritation, swelling (edema), itching (pruritis), burning, and pain via the analgesic affect.

The invention acts as an anti-fungal (fungistatic or fungicidal) device via cold (heat absorbing) technology introduced by the device (shell and filler), possibly by acting as an HSP 90 inhibitor (heat shock inhibitor) or cold shock inducer and acts to reverse yeast morphology, thus inhibiting any temperature sensitive component of a pathogen or the pathogen (in its entirety) by lowering the temperature of the body cavity tissue which reduces filamentous growth of *Candida* species, halting and curing VVC outright. VVC and BV form biofilms, making the conditions more difficult to treat, thus the device's cooling effect, along with the optional application of an agent in a coating compound such as those listed above, will provide additional mechanisms to eradicate infectious conditions in body cavities. The present invention disrupts the adjacent biofilm and modifies the body cavity temperature to that below about 30° C., to approximately 20-28° C. for about 30 minutes or longer, to allow penetration of hydrogen peroxide, lactic acid hydrogel, or some other agent to take effect. Biofilms disintegrate under temperatures of 30° C. and have 100 fold fewer bacterial colonies at these lowered temperatures, thus showing that some bacterial growth is temperature dependent.

Increasing the thermal conductance and cooling capacity via the addition of a SS sleeve or SS particles impregnated into the shell of the device create an effective BV or VVC biofilm dissolving function, and prolongs the duration of cooling. The introduction of a cooling, temperature reducing device to a body cavity which cures infections is novel to the industry. The use of a temperature reducing (heat transferring) intra-vaginal device for the purpose of inhibiting the filamentous, disease form of *Candida* yeast species, forcing the yeast to live in their dormant (non-VVC), ovoid, yeast form is novel to the industry. The combination of adding a compound coating, to one or more of the above mechanisms, is novel to the industry since no drug delivery devices use cooling as a component of their curative or therapeutic benefit. No device serves as a substance retention device with a cooling component for the purposes described herein.

In an embodiment, an optional SS sleeve is added to the device to disrupt a pathogen's biofilm more quickly and effectively via the cooling effect (tissue temperature reduction). In addition, a biofilm may be disrupted simply by the mechanical separation of the body cavity walls via insertion of a device.

The following Example 1 is provided:

Introduction

An office based proof of concept study was conducted by Dr. Kimberly Cull M.D. in 2009 with 20 of her patients who agreed to test the hypothesis that an intra-vaginal cooling device could relieve the symptoms associated with yeast vaginitis such as itching, burning, swelling, and pain, and reduce the need for anti-fungal medicines. Scientific evidence is substantial in showing the analgesic effect of applying cold compresses to inflamed, bruised, or swollen tissue. The mechanism of action is that of vasoconstriction which reduces the amount of exudate (fluid) egress into damaged tissue. Furthermore, it is well accepted that warmth often caused by tight fitting clothing and moisture are needed for the proliferation of yeast. In fact, it is the loss of nutrients, possibly as a result of *lactobacillus* (the 'good' bacteria) destruction from antibiotic exposure (lowering pH) that can cause yeast to 'morph' into their more virulent 'filamentous' form and become invasive, resulting in the infection known as yeast vaginitis, even at normal body temperatures. By altering one of the conditions necessary for yeast growth (temperature) with an intra-vaginal cooling device, it is hypothesized that yeast replication can be reduced, suppressing this invasive growth of yeast that causes the destruction of tissue, resulting in inflammation, pH changes, exudate and swelling. The adjacent tissue's ambient temperature was modified by introducing a cooling device into the vagina.

Background

Yeast vaginitis is a result of an overgrowth of *Candida albicans, Candida torulopsis, Candida glabarata*, or rarely, *Candida Krusei*, alone or in some combination. This study proposed that modifying one of the ambient conditions could prevent a full blown infection or treat the condition outright. The ambient conditions that predispose to yeast vaginitis are heat, moisture, immune compromise, antibiotic destruction of favorable micro-flora such as lactobacilli, trauma, pregnancy, estrogen deficiency and uncontrolled diabetes among others.

Yeast cannot grow well under 'cooler' conditions, among other conditions already mentioned. Laboratory guidelines for culturing yeast uses a temperature of 36° C. as the lowest minimum temperature to encourage growth. A useful analogy would be that of making bread from flour, water and yeast cultures. Yeast cultures are dissolved in warm water (95° F.) and the dough kept warm, otherwise, there will be no yeast multiplication, which is essential for the production of carbon dioxide gas which makes the dough rise. With that principle in mind, yeast vaginitis can be ameliorated by keeping the surrounding tissue cooler, reducing the ability of yeast to multiply into an 'overgrowth' situation which causes the inflammation resulting in the symptoms of itching, burning, swelling, discharge and pain.

The study is a compelling example of the possibility that yeast vaginitis can be prevented, treated and even cured without the introduction of chemicals. Furthermore, it is logical to assume that all species of yeast (four species are known to inhabit the vagina) are affected by temperature, while most oral and OTC antifungal creams only treat one species of yeast.

Materials and Methods

Twenty patients were recruited for participation. Each presented for evaluation with the symptoms of itching, vaginal discharge, pain or burning of the vagina. Ages ranged from 18-45, and all were experiencing normal monthly menstrual cycles. Participants were given a questionnaire to complete pre and post treatment. Histories and physicals ruled out confounding conditions, such as sexually transmitted diseases (STD's), bacterial vaginosis, atrophic vaginitis and urinary tract infections (UTI's). Tests such as screening for gonorrhea and chlamydia, nitrazine test, microscopic exam of the vaginal discharge to determine the presence of hyphae or clue cells, were performed in all cases. A urinalysis (UA) dipstick was used to rule out cystitis or pregnancy, as well. All participants were current with pap smears. No trichomonas, bacterial vaginosis, UTI's, pregnancy, or STD's were found. Cultures for yeast returned positive in 15 of the participants. All of the participants responded to a questionnaire (pre and post treatment).

The Treatment Device (TD) used was a frozen tampon. Each participant placed the TD intra-vaginally. After one hour, or sooner, if no additional cooling sensation was noted, participants removed and discarded the TD. If desired, they were could repeat the above instructions with a second TD.

Results

Of the 20 women who agreed to participation in this study, all completed the questionnaires, both pre and post treatment. Even though five of the participants failed to have a culture positive for yeast growth, they sufficiently qualified as suffering from yeast vaginitis based on subjective questioning and other physical findings as identified on physical exam. All participants answered positively to experiencing itching, discharge, burning, pain with sexual intercourse, or irritation and negatively to recent antibiotic use or antifungal use.

Eighteen participants thought that insertion of the TD was not painful, but some comments included that it was awkward and more painful, if swelling was present. Two participants thought that insertion was somewhat difficult, but they also had the most amount of swelling as noted on physical exam. Wetness was experienced by all 20 participants as a result of the melting of the TD.

All responses were positive as to relief of symptoms. Itching and burning were improved in all participants within 30 minutes of insertion, which continued after removal. Ten participants resumed sexual activity within 3 days after use of the TD; 6 within 5 days, and 4 within 7 days.

All participants responded that they their condition improved or helped after the therapy. Sixteen thought they were completely cured of yeast vaginitis, while four were not sure if they were completely cured, but still reported much improved symptoms. None resorted to additional therapies or medicines. All of the participants answered affirmatively that they would consider this mode of therapy in the future, but would prefer not to have dampness as a side effect.

Conclusions

Ambient conditions in the vagina are tantamount to yeast proliferation and can be reduced via the alteration of certain ambient conditions. Disease or infections need certain conditions, substrates, nutrients, temperatures, predisposing factors to manifest and cause harm. While we cannot always prevent exposure to harm, we can easily alter one essential 'factor' for disease progression.

The following is Example 2 is provided.

Reversing Yeast Morphology with a Cooling Device

Controlling *Candida albicans* via Physical Inhibition of HSP 90 Function.

Author: Kimberly Cull, M.D.

Background

VulvoVaginal Candidiasis (VVC) is the second most common form of infectious vaginitis, accounting for 30-35% of all cases, while Bacterial Vaginosis (BV) accounts for the diagnosis in 40-45% of women who present with vaginal complaints. VVC symptoms include vulvar and vaginal itching, burning, swelling, erythema, and pain, with or without discharge, and with a normal acidic pH of 3.5-4.5. On the other hand, BV is diagnosed based on the finding of normal flora in the presence of clue cells, elevated pH, a malodorous discharge, and relative lack of an inflammatory response. Biofilms appear to be a component of many forms of pathological 'Vaginitis-like' conditions. Other types of vaginitis include aerobic vaginitis, desquamative inflammatory vaginitis, purulent vaginitis, and streptococcal vaginitis [33], among other noninfectious causes of vaginitis. Vaginal atrophy from estrogen deficiency and radiation induced vaginitis are two non-infectious forms of vaginitis.

*Candida albicans* accounts for 85-90% of all cases of VVC [24]. Other species of *Candida* that can cause vulvovaginitis (VVC) include *C. tropicalis, C. glabrata, C. krusei,* among others. Risk factors for the development of VVC include excess heat, moisture, antibiotic destruction of favorable microflora such as *lactobacillus*, diabetes, immune-compromise, pregnancy, and oral contraceptive use [24]. The risk of disseminated candidiasis in cases of immune-compromise underscores the need for non-toxic, fast, and preventative means for treating this vexing and recurring condition, for which current therapies are effective only 70-80% of the time. These prescription and over-the-counter (OTC) topical anti-fungal medications result in significant toxicities from yeast cell wall destruction with the release of enzymes, inflammatory immune responses, and allergic skin reactions from caustic ingredients in the topical medications. This causes delays in symptom relief and subsequent cure, potential interactions with systemic medications, and the risk of anti-fungal drug resistance due to repetitive or inaccurate therapies.

The focus of this scientific review is to show how *Candida* HSP (heat shock protein), specifically HSP 90, is the target for treating both the etiology and symptoms associated with VVC, primarily by reducing the heat shock response or invoking a cold shock response, thus reversing the morphological switching that plays the fundamental role in yeast virulence. 'Heat shock protein's (HSP) are molecular chaperones whose production is increased as a result of environmental stressors such as elevated temperature and 'oxidative' inflammation. This review will address the link between HSP 90, yeast morphological states, signal transduction pathways, tissue destruction, and excess heat in body cavities. Furthermore, the author will illustrate a molecular mechanism of action explaining why an intra-vaginal cooling device ameliorates symptoms immediately and reverses yeast morphological pathobiology, curing the condition known as VVC, without medication or chemicals.

Morphological States of *C. albicans* and Molecular Pathways

*C. albicans* exists in three morphological states, yeast, psuedohyphae, and hyphae. The latter two, collectively considered 'filamentous', account for *Candida*'s virulence, and are the two forms responsible for VVC, among other human fungal infections. *C albicans*' morphologies are enormously plastic, able to change readily from one form to another [6]. Depending on environmental conditions such as temperature, nutrient depletion, pH or CO2 elevation, the yeast can change shape in order to survive hostile or changing environments. The requirement for temperature elevation to induce morphogenesis has remained enigmatic [1]. In vivo, all three morphologies might coexist at a single site of infection [2]. This phenotypic switching clearly plays a role in virulence [8]. At higher temperature and pH, the hyphal form predominates [9]. At 37 C and with exposure to serum, unbudded yeast converts to hyphal forms, whereas at 35 C and neutral pH, both pseudohyphal and hyphal forms predominate. At 30 C (86 F), and a pH 4.0 or less, dormant, yeast forms exist [10].

The yeast-to-hyphal or bud-to-hyphal transition (BHT) is triggered by a wide range of environmental factors such as carbohydrates, amino acids, salts, pH changes, temperature increases (or decreases), nutrient depletion, growth within a matrix (biofilms)[38]. In *C. albicans*, this BHT is a result of signal transduction pathways [39]. The two most studied of these are the mitogen-activated protein kinase (MAPK) which regulates cell wall integrity as a result of environmental perturbations (stress) and the cAMP-protein kinase A (PKA) pathway which is the nutrient sensing pathway or the 'fermentable growth medium' (FGM) pathway [40] and possibly a temperature integrating pathway via the Ras 1 cAMP PKA [1,43].

The other pathways include an amino acid sensing, ammonium sensing, mechanosensing, and the Tup1-Nrg1 mediated pathway that REPRESSES filamentation independent of the cAMP-PKA (EFg1) or MAPK(Cph1) pathways [41,42]. Nrg 1 is a DNA binding protein that represses filamentous growth in *C. albicans*, probably acting through co-repressor Tup 1[62]. Braun et al. (2001) showed that growth in serum at 37 C resulted in a reduction in Nrg 1 mRNA, suggesting that filamentous growth is induced by down-regulation of Nrg 1[62], making it possible that lowering temperature causes an up-regulation of Nrg 1 which represses filamentation. The Tup 1-Nrg 1, MAPK, mechanosensing pathways warrant closer examination in relation to the 'physical' temperature conditions which impact *C. albicans*' morphologic switching, in addition to the cAMP-PKA pathway's potential dual role in both nutrient and temperature sensing.

To date, there have been identified 16 out of 480 molecules tested which inhibit the cellular signaling that block the BHT. These inhibitors affect protein kinases, protein phosphatases, Ras signaling pathway (nutrient sensing), G-protein coupled receptors (GPCR), calcium homeostasis, nitric oxide, and guanylate cyclase [41]. The temperature effect on GPCR is receptor specific, as in many mammalian receptors, a decrease in temperature results in up to a six fold increase in receptor expression [44]. The explanation that protein production is slowed (receptors down-regulated) by cooling is thought to be dependent upon not overloading the translocation machinery, protein processing, or intracellular trafficking. Thus, lowering temperatures could reduce proteolytic activities [45] or up-regulate cold shock proteins such as chaperones[44]. The focus of this research proposal is to learn more about the link between physical 'temperature' reduction as it relates to reversing yeast morphology, inhibiting or blocking yeast filamentation and how the BHT is dynamic and reversible, which allows *C. albicans* the ability to survive and thrive in many host conditions and substrates.

Environmental Sensing in Fungi

Several types of environmental sensing responses in fungi have been identified. They include responses from low oxygen, nutrient deprivation, osmotic stress, and contact sensing. Contact sensing in fungi regulates differentiation which is crucial for virulence [54]. *C. albicans*, contact sensing results in the formation of invasive growth[46]. This mechano-sensing involves mechanosensitive (MS) ion channels, G-protein couple receptors (GPCR), and integrins. These MS ion channels open in response to physical stimuli that affect the membrane [47,48]. A biologic result occurs as a result of a mechanical stimulus[42]. *C. albicans* exhibit a behavior termed thigmotropism which result in the reorientation of hyphae in response to ridges and are believed to be a result of MS channel function[55]. This thigmotropism might guide invading hyphae towards gaps between cells, facilitating the tissue penetration necessary for virulence[42] Hence, *C. albicans* cells sense the properties of a surface and produce characteristic biological responses [42].

GPCR are also implicated in mechanosensing. They are activated by light absorption, ligand binding, and mechanical forces described as mechanical stretching [58], shear stress [57], hypotonic stress, and membrane fluidity [42]. For instance, if a mutant *C. albicans* lack the GPCR Gpr1p, filamentation in response to contact is defective whereas their response to other environmental cues is normal [49-51]. These bud-to-hyphal (BHT) defects were stronger on solid hyphal inducing media compared to liquid media.[39]. This supports the observation that hyphal forms are more capable of solid tissue (vagina) penetration, whereas the yeast bud forms are more suited for dissemination through the bloodstream. Likewise, on solid surfaces, *C. albicans* can form biofilms [52]. Overall, little direct investigation of how mechanical forces influence GPCR function has been performed [42].

Integrins are transmembrane signaling proteins that respond to forces exerted perpendicular to the surface of a cell membrane [59]. Using atomic force microscopy, the fungal cell wall undergoes an oscillating motion whose frequency is temperature-dependent and results in a biologic activity [60]. Thus, temperature changes create mechanical perturbations that change the vibrational energy of the cell membranes, triggering integrins, GPCR's, or MS ion channels to perform their biological functions. A useful 'physics' analogy would be that of cold causing contraction of the molecules of gas, liquid or solid materials, whereas heat causes the expansion of these same physical states of matter. Regardless, fungi have evolved to adapt to many environmental conditions of which temperature reigns as important candidate for manipulation.

Heat Shock Proteins as Molecular Controllers of Morphology

Heat Shock Proteins (HSP's) are the most abundant proteins in microbes and humans, and act as molecular chaperones, serving both housekeeping functions and adaptation for survival in hostile conditions, such as surviving the mammalian host's immune system. Yeast HSP 90 is essential for the viability of yeast [12]. As a molecular chaperone, HSP 90 ensures the correct conformational activity, localization, and proteolytic turnover of a range of proteins that are involved in three processes: cell growth, differentiation, and survival [27,28,29]. In 2004, Albarrag opined that HSP 90 may play role in the pathogenesis and virulence of *C. albicans* [11]. In fact, HSP 90 is the key mediator of *C. albicans*' pathobiology, controlling nearly all facets including morphogenesis, biofilm formation, virulence, and anti-fungal drug resistance [20][21]. In non-stressed cells, HSPs are present in low concentrations; but when stressed, they accumulate to high levels [4]. According to Bergman and Segal, HSP 90 suppresses phenotypic variation under normal conditions, but releases this suppression of variation when functionally compromised [25]. Thus, in conditions of elevated temperature, these proteins increase 5-6 fold, thus explaining the 'heat shock response' [3]. This leads to a switch from yeast to 'filamentous' forms which are considered invasive and promote tissue penetration which is explains most of the symptoms found in VVC [2].

Yeast HSP 90 'reversibly' governs morphogenetic transition from yeast to filamentous growth [1]. This transition is regulated by environmental cues such as exposure to serum, pH and CO2 elevation, nutrient limitation, that is contingent upon elevated temperature to induce morphogenesis [15] [16]. In other industries, an example of yeast activity or growth as a function of temperature can be shown with the fermentation process of *S. cerevisiae* (84% homologous to *C. albicans*). Yeast cells are exposed to complex and varied carbon sources, and 'stressed' by anaerobic growth, high specific gravity, ethanol, and temperature 'shocks'. Whereas, during times of storage for extended periods of time, yeast is kept dormant at lowered temperatures. [3].

In 2009, Shapiro showed that by compromising yeast HSP 90 PRODUCTION, not FUNCTION via biochemical, pharmacologic, or genetic pathways, the temperature and serum exposure requirement could be mitigated, causing a yeast to filamentous switch. [1]. Shapiro further demonstrated that in liquid rich media at 30 C (86 F), *C. albicans* exists as budding yeasts, and that even with exposure to serum, this temperature did not cause filamentation. She suggested that Yeast HSP 90 is essential for morphogenesis which makes targeting HSP 90 production the ideal therapeutic strategy [1]. In fact, inhibition of HSP 90 'function' in *C. albicans* blocks the emergence and maintenance of resistance to azoles, enhancing their efficacy in vivo [7]. Thus, exposing *C. albicans* to a 'cooling' environment after a 'heat shock' resulted increased HSP 90 production, means that reducing the temperature either impairs HSP 90 function or that another pathway has become activated such as the 'cold shock response'. Since temperature elevation raises HSP 90 production via up-regulation that occurs when cells are heat shocked from 25 C to 37 C for 30 minutes [34], inhibiting HSP 90 function via tissue temperature reduction for 30-40 minutes should reverse the 'filamentous' forms back to the non-disease causing 'yeast' morphologies, since this morphological process is reversible. The answer or conclusions await further study More confirmation of this temperature 'essentiality' was shown in another study conducted by Shapiro in 2012, an HSP-90 co-chaperone (Sgt1) was identified that also coupled temperature sensing with morphogenesis. It was shown that by inhibiting HSP 90 function, and to a lesser extent, Sgt1 function, the *Candida* susceptibility to azoles and echinocardins was enhanced, creating a fungicidal, rather than fungistatic combination of these anti-fungal drugs, and reduce biofilm resistance at 30 C [5]. By reducing the temperature to 30 C, Sgt1 and HSP 90 activities were reduced, verifying that the virulence of *C. albicans* is dependent on temperature elevation, making the author's theory that virulence is diminished with temperature reduction. Likewise, biofilms begin to form at 30 C and above and start to disintegrate at temperatures below 30 C and under conditions of less energy and diminishing nutrients [23]. Thus, temperature reduction via an intra-vaginal cooling device could have a potential role in BV and aerobic vaginitis since both are thought to be resistant to therapy as a result of their protective biofilms which are adherent colonies of microorganisms, held together by a matrix of polysaccharides, proteins, and nucleic acids and which have a predilection for skin and mucosal surfaces [23].

Thus, lowering tissue temperature acts as an HSP 90 inhibitor or blocker by reducing filamentous growth, forcing or pushing it back to the 'yeast' form which is the dormant, co-inhabitant state of *Candida* species. This 'reversibility of morphology' feature is also why the addition of heat can restart the virulent morphological cycle that causes VVC.

Combined Human HSP 70 and Yeast HSP 90 Explains VVC Symptom

Yeast HSP 90 is located on cell wall surfaces at different concentrations influenced by environmental and nutritional conditions with large concentrations at the tips of the hyphae. The tips of the hyphae play a role in virulence since this is the site of enzyme secretion which results in tissue penetration, protein and lipid destruction, and host responses, as a result [13]. Host responses in VVC include vaginal discharge, itching, burning, swelling, and pain. This is due to a combination of the body's immune response to the enzymatic destruction of tissue resulting in inflammation, which then results in human HSP 70 up-regulation from this oxidative stress. HSP 70 was recently recognized as one of the antimicrobial proteins present in the vagina [35, 36]. Inflammation occurs as a result of an activation of various signaling molecules involving prostaglandin and arachidonic acid production as a result of Phospholipase A. Both of these further induce the heat shock response leading to increased HSP synthesis [26]. The initial increase in heat triggers the yeast HSP 90 to 'morph' into filamentous forms, which then results in inflammation which induces both the host and the pathogen to respond with increased HSP production creating a dynamic, vicious cycle of growth and destruction.

Likewise, in 1998, it was discovered that HSP 90 and HSP 70 (Genc, 2006) cause the release of nitric oxide, a smooth muscles relaxer, vasodilator, and potent inhibitor of platelet aggregation [17]. Nitric oxide has an antimicrobial activity against a wide variety of microorganisms [37]. This overproduction of nitric oxide was demonstrated in the murine model of oral candidiasis [14]. HSP 90 also activates the kinin-forming cascade leading to bradykinin release, causing edema and more vasodilation, and explains the notable swelling found with VVC. By inhibiting HSP 90, the nitric oxide formation is decreased with a resultant decrease in cell damage, exudative discharge, erythema, and swelling [18]. It has long been established that applying cooling packs to reddened, swollen, inflamed, and sore tissue will lessen those symptoms, and now we have a plausible molecular explanation to accompany the well-known role of coolness in producing vasoconstriction, reducing fluid egress into tissue.

To summarize, both host cells and microbes are confronted with dramatic alterations in living conditions during an infection (i.e. vasodilation from nitric oxide, bradykinin release, phospholipase and proteinase production, histamine release, hemolytic activity, adhesion to vaginal epithelial cells causing biofilms, inflammatory/immune cell response, edema, and erythema). ALL of these contribute to further alterations in pH, CO2 production, increased heat and inflammation. Thus, reducing the surrounding tissue temperature can improve both the signs and symptoms (caused by the inflammation), as well as 'curing' VVC by pushing 'filamentous' *Candida* growth back to the dormant 'yeast' forms or by blocking the continual 'filamentous' transformation, allowing the host immunity to repair and heal the traumatized tissue. Thus, by lowering the temperature of the yeast environment, both human HSP 70 and *Candida* HSP 90 are relegated to their 'housekeeping' rather than cytoprotective 'heat shock' roles, caused by exposure to temperature elevations.

Immune Response to HSP 90

HSP's are major antigens and induce a very strong humoral and cellular immune response [4]. Many of the cellular responses were mentioned previously. In mycology, HSP 90 has been identified as a potential target for immunotherapy, since the activation HSP 90 was inhibited by a monoclonal antibody to HSP 90 known as Mycograb [4]. Mycograb is a human recombinant protein that recognizes the middle domain of fungal HSP 90. When combined with the antifungal drug amphotericin B, it has been shown to reduce mortality in systemic *candida* with an 84% response rate for multiple species of yeast, including *C. albicans, C. glabrata,* and *C. tropicalis* [30]. This illustrates the presence of 'heat shock proteins' in all or most species of pathogenic yeast and supports the author's theory that all species of *Candida* that cause VVC will respond to a cooling device, not just *C. albicans*.

Autoimmune or Chronic Disease Connection to HSP 90

"Provoked vestibulodynia, the most common form of vulvodynia (unexplained pain of the vulva), is a prevalent, idiopathic pain disorder associated with a history of recurrent candidiasis (VVC)" [22]. In a subset of female mice subjected to recurrent *Candida albicans* infections, they developed a mechanical allodynia (painful hypersensitivity to touch) of the vulva. This subset also exhibited hyperinnervation with peptidergic nociceptor and sympathetic fibers. Long lasting allodynia was also observed after a single, extended *Candida* infection, as well as repeated vulvar inflammation induced with a mixture of fungal antigens [22]. Tolerance to self antigens may be distorted by frequent encounters of the immune system with microbial antigens with high similarity to self [19]. Because Yeast HSP and human HSP 90 share similarity in composition, and due to HSP wide distribution and their homology among different species, it is not surprising that autoimmune phenomena can be explained "as when HSP expression and HSP immune responses are regulated inappropriately."[4] Thus, ongoing inflammatory processes, repetitive exposure to HSP and microbial antigens, with continued immune responses can explain why chronic diseases such as vestibulitis or vulvodynia exist, and may represent an autoimmune phenomenon. It is due to the structural homology between microbial and 'self' HSP [4]. Preventing and reversing these antigenic exposures, without the need for chemicals found in antifungal therapies, is the basis for a vaginal cooling device as treatment for VVC.

Conclusion and Future Considerations

Being able to treat the etiology of VVC by changing yeast morphologies and disrupting biofilms via temperature reduction with a fast, non-toxic, and simple device whose 'cooling' mechanism also relieves the concomitant symptoms such as itching, burning, swelling, and pain on contact, is the basis for this review of the literature. A 'Proof of Concept' study was conducted by the author in 2009 on twenty patients each suffering from an uncomplicated case of VVC. Each used a tap water saturated, frozen tampon for less than two hours, and everyone experienced immediate relief, and none resorted to additional therapies.

The need exists to complete more detailed studies with the author's patent pending polyurethane or silicone medical grade device, filled with a freezable gel, to determine the appropriate degree of temperature reduction, duration of use, and number of times (dosage) needed which results in a cure of VVC while simultaneously ameliorating the symptoms of VVC. With the availability of a rapid, sensitive immunochromatography test (ICT) known as the CandiVagi assay (SR2B, Arville, France), the study will be able to discriminate between *Candida* carriage and *Candida* infection, with the specificity to exclude any women with either bacterial or trichomonal vaginitis [31]. Yeast cultures can determine the exact species and further validate the amount of growth or severity of *Candida* infection, which will be correlated with clinical exams, cervicovaginal lavage to measure host immune response as well as quantifying levels of lactobacilli, and other vaginal microflora via PCR. Expression levels of a filament-specific transcriptional regulator can determine *C. albicans* morphology and virulence according to Carlisle et al [49]. Using Transmission Electron Microscopy by fixing *C. albicans* in the McDowell-Trump fixative, it will be possible to show the microstructural and gross morphological changes in yeast cells, after exposing yeast to varying temperatures [53]. HSP 90 levels and function should be quantified and qualified with regard to temperature fluctuations.

Intravaginal sensors such as those used by Hill et al (2005) to measure vaginal oxygen and carbon dioxide levels during menses can be used. Physiologic levels are atmospheric in the vagina, with a slight transient increase in oxygen levels with tampon insertion. Carbon dioxide levels remained unchanged with tampon insertion [32]. These Neotrend sensors are fiber optic based units and less than 0.5 mm in diameter and 23 mm in length. These sensors record temperatures, pH, pCO2, pO2 levels continuously [32], elucidating the physiologic aspects of cooling in a body cavity. Other parameters and diagnostic tools may be considered as the data is collected and analyzed. Biofilm disruption as a result of temperature reduction should be addressed, either separately or in a combined microbiologic and clinical trial. The existence of reconstituted human vaginal epithelium (RHVE) used by Pietrella et al [61] for evaluation of the vaginal immune response to *C. albicans*, may be useful in reconstructing biofilm formation.

Patient questionnaires after clinical evaluation and examinations are performed will be used prior to device insertion, during the treatment, immediately after-wards, within 24 hours, at one week, and one month later. Results from the questionnaires, clinical assessments, and test results will be correlated to determine the device's efficacy and help elucidate a mechanism of action.

The foregoing descriptions of specific embodiments and examples of the present invention have been presented for purposes of illustration and description. They are not intended to be exhaustive or to limit the invention to the precise forms disclosed, and obviously many modifications and variations are possible in light of the above teachings. It will be understood that the invention is intended to cover alternatives, modifications and equivalents. The embodiments were chosen and described in order to best explain the principles of the invention and its practical application, to thereby enable others skilled in the art to best utilize the invention and various embodiments with various modifications as are suited to the particular use contemplated. It is therefore to be understood that within the scope of the appended claims, the invention may be practiced otherwise than as specifically described herein.

What is claimed is:

1. A method of disrupting and inhibiting the growth in a body cavity of a pathogen, comprising repeating, until a therapeutic effect is achieved the steps of:

providing a device comprising an outer shell having a wall that encloses a chamber formed therein and an inner cooling or freezable filler material that substantially fills the chamber, wherein the outer shell is formed from a flexible expandable polymer that is sized and adapted for intimate contact with walls of the body cavity, wherein the outer shell further comprises stainless steel particles impregnated into the outer shell, and wherein the outer shell fully contains and encloses the inner cooling or freezable filler material, and wherein upon filling the chamber with the cooling filler material the polymer is capable of expanding and wherein upon contact with walls of the body cavity the polymer is capable of flexing, and wherein the device does not include a second chamber for enclosing or accepting any additional contents, and wherein the device does not comprise external circulation of the inner filler;

cooling or freezing the device;

inserting the cooled device into the body cavity;

allowing the device to remain in the body cavity for a period of time sufficient to promote a condition in the pathogen selected from: dormancy, changed morphology, cessation of growth, disruption of a biofilm created by the pathogen, and any combination thereof; and removing the device from the body cavity.

2. The method of claim 1, wherein the pathogen is a yeast.

3. The method of claim 2, wherein the yeast is genus *Candida*.

4. The method of claim 1, wherein the outer shell comprises a thermoplastic polymer or like material.

5. The method of claim 1, wherein the filler comprises a material selected from the group consisting of saline, water, hydrogel, and any combination thereof.

6. The method of claim 1, wherein the period of time is between 30 and 60 minutes.

7. The method of claim 1, wherein the steps are repeated at least two times.

8. The method of claim 1, wherein the steps are repeated at least three times.

* * * * *